(12) United States Patent
McCormack et al.

(10) Patent No.: US 9,175,139 B2
(45) Date of Patent: Nov. 3, 2015

(54) ALKOXY GROUP-CONTAINING SILICONES WITH REACTIVE FUNCTIONAL GROUPS OF DEFINED REACTIVITY

(71) Applicant: Wacker Chemical Corporation, Adrian, MI (US)

(72) Inventors: Timothy McCormack, Ypsilanti, MI (US); Daniel Calimente, Saline, MI (US)

(73) Assignee: Wacker Chemical Corporation, Adrian, MI (US)

( * ) Notice: Subject to any disclaimer, the term of this patent is extended or adjusted under 35 U.S.C. 154(b) by 0 days.

(21) Appl. No.: 14/217,789

(22) Filed: Mar. 18, 2014

(65) Prior Publication Data

US 2015/0267004 A1    Sep. 24, 2015

(51) Int. Cl.
C08G 77/26    (2006.01)
C07F 7/08    (2006.01)

(52) U.S. Cl.
CPC .............. *C08G 77/26* (2013.01); *C07F 7/087* (2013.01); *C07F 7/0872* (2013.01)

(58) Field of Classification Search
None
See application file for complete search history.

(56) References Cited

U.S. PATENT DOCUMENTS

| | | | | |
|---|---|---|---|---|
| 2,793,223 A * | 5/1957 | Merker | ................ | 556/440 |
| 2,956,044 A * | 10/1960 | Merker | ................ | 526/279 |
| 4,208,503 A * | 6/1980 | Martin | ................ | 528/14 |
| 4,336,309 A * | 6/1982 | Jackel et al. | ................ | 428/447 |
| 5,280,098 A * | 1/1994 | Witucki et al. | ................ | 528/17 |
| 5,366,768 A * | 11/1994 | Kasari et al. | ................ | 427/407.1 |
| 5,516,858 A * | 5/1996 | Morita et al. | ................ | 525/478 |
| 5,635,546 A * | 6/1997 | Rich et al. | ................ | 523/176 |
| 5,650,474 A * | 7/1997 | Yamaya et al. | ................ | 528/12 |
| 5,663,269 A * | 9/1997 | Chu et al. | ................ | 528/14 |
| 5,814,703 A | 9/1998 | Yamaya et al. | | |
| 5,945,172 A * | 8/1999 | Yamaya et al. | ................ | 427/503 |
| 6,048,910 A * | 4/2000 | Furuya et al. | ................ | 522/86 |
| 6,100,332 A * | 8/2000 | Yoshikawa et al. | ................ | 525/101 |
| 6,344,520 B1* | 2/2002 | Greene | ................ | 525/100 |
| 6,713,559 B1* | 3/2004 | Armbrust et al. | ................ | 525/100 |
| 6,713,586 B2 | 3/2004 | Greene | | |
| 6,864,340 B2* | 3/2005 | Levandoski et al. | ................ | 528/34 |
| 7,238,768 B2* | 7/2007 | Hupfield et al. | ................ | 528/38 |
| 7,408,012 B1* | 8/2008 | Kneafsey et al. | ................ | 526/279 |
| 7,598,314 B2* | 10/2009 | Lee et al. | ................ | 524/588 |
| 2004/0175637 A1* | 9/2004 | Tong et al. | ................ | 430/58.2 |
| 2006/0247408 A1* | 11/2006 | Crivello | ................ | 528/33 |
| 2011/0201751 A1* | 8/2011 | Liu et al. | ................ | 524/837 |

FOREIGN PATENT DOCUMENTS

| | | |
|---|---|---|
| EP | 1086974 A1 | 3/2001 |
| EP | 1359182 A1 | 11/2003 |
| WO | 2013099548 A1 | 7/2013 |

OTHER PUBLICATIONS

PCT International Search Report, Date Completed in European Patent Office May 26, 2015, Application No. PCT/EP2015/054976, 11 pages.

* cited by examiner

*Primary Examiner* — Robert S Loewe

(74) *Attorney, Agent, or Firm* — Brooks Kushman P.C.

(57) ABSTRACT

Organopolysiloxanes having a greater degree of defined reactivity through epoxy, isocyanate, anhydride, amino, carboxy, and (meth)acrylate groups are prepared by cohydrolytic condensation of reactive group-containing precursors and other condensable precursors in amounts such that the reactive organopolysiloxanes product contains on average more than two reactive groups, less than 20% by weight of alkoxy groups, and a proportion of non-reactive optionally substituted hydrocarbon groups such that the ratio of non-reactive hydrocarbon groups to Si atoms is greater than 1.

20 Claims, No Drawings

ALKOXY GROUP-CONTAINING SILICONES WITH REACTIVE FUNCTIONAL GROUPS OF DEFINED REACTIVITY

BACKGROUND OF THE INVENTION

1. Field of the Invention

The present invention pertains to reactive organopolysiloxanes (silicones) bearing alkoxy groups and reactive organic groups which dominate the overall reactivity of the reactive silicone. The reactive silicones are prepared through hydrolytic condensation of hydrolyzable precursors. The invention further pertains to curable compositions containing the reactive organopolysiloxanes, and to their use, particularly in coatings and encapsulants.

2. Description of the Related Art

Silicones having reactive organic functional groups such as hydroxyalkyl, aminoalkyl, isocyanatoalkyl and the like are known. Such reactive silicones may be prepared, for example, by hydrosilylating an ethylenically unsaturated compound also bearing a desired reactive group, for example allylamine or isocyanatoethylmethacrylate with a silane or polysiloxane bearing silicon-bonded hydrogen ($\equiv$Si—H). A desirable characteristic of these reactive silicones is that they react exclusively through the reactive organic functionality, or in other words, have "defined reactivity." However, a disadvantage is that more expensive Si—H functional organosilicon compounds must be used to prepare them, and that ethylenically unsaturated compounds bearing the desired reactive group may not be available, may not have the desired stability, or are available at only relatively high cost.

A further disadvantage is that hydrosilylation generally employs a noble metal hydrosilylation catalyst, generally a platinum-based catalyst, which adds to the expense. If the hydrosilylation reaction is not complete, unreacted ethylenically unsaturated reactants must be removed, e.g. by subjecting the product mixture to stripping or vacuum, which is not always effective unless the temperature is raised. For some reactive groups, however, raising the temperature is contraindicated, as the reactive functional groups may react or condense. Furthermore, if the final product contains unreacted Si—H groups, these may give rise to storage problems, especially if water is present. Reaction with water can liberate explosive hydrogen gas.

In U.S. Pat. No. 5,814,703, highly branched silicones having aminoalkyl, epoxyalkyl, or ethylenically unsaturated groups are prepared, not by hydrosilylation, but by hydrolytic condensation of a functional dialkoxysilane or trialkoxysilane with a non-functional dialkoxysilane or trialkoxysilane, optionally together with tetra-alkoxysilanes. These highly branched reactive silicones contain minimally 10 mol percent of "T-units," $RSiO_{3/2}$, which form branching sites. Moreover, they contain a limited amount of non-functional hydrocarbon groups relative to the number of silicon atoms. Due to these requirements, and as a result of the preparation method, in addition to the desired reactive functional group, the products contain a large quantity of non-hydrolyzed alkoxy groups. These reactive silicones may be used to form hard coatings when admixed with a non-functional polymer resin, or preferably, a reactive, crosslinkable polymer resin.

It has been found, however, that reactive silicones such as those disclosed in U.S. Pat. No. 5,814,703, have numerous drawbacks. First, the relatively high proportion of alkoxy groups allows the silicone, once the organic reactive groups have reacted, to further crosslink in the presence of moisture, which is unavoidable in coatings and articles intended for normal use. Thus, the chemical bonds formed are only partially the result of reaction of the intended organic functional groups. "Designed reactivity" under such conditions is impossible to achieve. Moreover, under conditions of high humidity, the alkoxy groups may react even prior to reaction of the organic functional groups, decreasing mobility of the growing polymer chains to the extent that a proportion of the functional groups may remain unreacted. Furthermore, the products, particularly when used in sections thicker than thin films, show evidence of cracking, shrinkage, and voids (from outgassing of condensation reaction alcohol) which may occur even as early as during initial cure. Such compositions are completely unsuitable as encapsulants for electronic devices, for example. Finally, these reactive silicones display poor compatibility with many polymers, as a result of which a homogeneous coating composition is difficult or even impossible to obtain, or which may be subject to phase-out into silicone-rich and silicone-poor regions in the cured product.

It would be desirable to provide reactive silicone polymers by a method which avoids hydrosilylation and its disadvantages, yet provides a greater degree of defined reactivity. It would be further desirable to provide reactive silicone resins which are flexible and exhibit little tendency to crack or develop voids during cure or thereafter, and which exhibit greater compatibility with organic polymers.

SUMMARY OF THE INVENTION

It has now been surprisingly and unexpectedly discovered that if the number of non-reactive silicon-bonded organic groups in a reactive silicone is increased beyond a ratio of 1 per silicon atom, and the residual alkoxy group content is kept below 20 weight percent, that a greater degree of defined reactivity, lesser tendency to crack during or after cure, and greater compatibility with organic polymers can be simultaneously obtained. This is achieved by synthesis of the reactive silicone by careful selection of the hydrolyzable precursor reactants such that the ratio of non-functional groups to silicon in the reactive silicone polymer is greater than 1:1, and the alkoxy content is less than 20 weight percent, while having a reactive functionality greater than 2 on average per molecule, this functionality selected from among epoxy, amino, anhydride, isocyanate, carboxylic acid, and acrylic functionalities.

DETAILED DESCRIPTION OF THE PREFERRED EMBODIMENT(S)

The reactive silicones of the present invention are prepared by the cohydrolytic condensation of alkoxysilanes or alkoxypolysiloxanes bearing reactive epoxy, amino, anhydride, isocyanate, carboxylic acid, or (meth)acrylic groups bound to silicon by Si—C bonds, with alkoxysilanes or alkoxypolysiloxanes bearing non-functional groups. The alkoxy functionality of the various reactants is selected so as to provide a low alkoxy content, less than 20 weight percent calculated as methoxy groups based on the total weight of the reactive silicone, preferably less than 18 weight percent, and preferably also in the range of 1 to 17 percent, more preferably 2 to 17 percent, and also 2 to 15 percent, and more than 1 non-functional group per silicon atom, on average, in the reactive silicone, more preferably on average 1.1 to 1.5 non-functional groups per silicon atom. If other than methoxy groups are present, the appropriate weight percents are calculated as if the alkoxy groups present were methoxy groups.

Most preferably, the reactive functional groups are supplied by hydrolytic condensation of an alkoxysilane bearing the desired functional group, for example glycidoxypropyltrimethoxysilane, glycidoxypropylmethyldimethoxysilane, or glycidoxypropyldimethylmethoxysilane, when, for example, an epoxy group is the desired reactive functionality. Amino, anhydride, carboxylic acid, acrylic, and isocyanato-functional silanes may be used in analogous fashion to prepare the respective functional silicones. Also, preferably, an alkoxysilane or alkoxypolysiloxane bearing non-functional groups, most preferably an alkoxypolysiloxane, optionally together with an alkoxysilane, is used to provide the non-functional groups.

By "non-functional" group is meant an organic group R with little or no reactivity under expected preparation conditions, and subsequently under curing conditions. Such groups are Si—C bonded, optionally substituted hydrocarbon groups, examples of which are alkyl groups, alkenyl groups (when the reactive group is other than a (meth)acrylic group), aryl groups, aralkyl groups, and alkaryl groups, where the alkyl groups may be linear or branched or cyclic. "Non-functional" groups do not include Si—O bonded alkoxy groups, Si—N bonded nitrogen-containing groups, and silicon-bonded halogen.

Suitable R groups are, for example, linear alkyl groups such as methyl, ethyl, propyl, butyl, pentyl, hexyl, octyl, decyl, dodecyl, octadecyl, etc., branched alkyl groups such as 2-butyl, and ethylhexyl; cycloalkyl groups such as cyclopentyl, cyclohexyl, methylcyclohexyl, and cyclohexylmethyl; alkenyl groups such as vinyl, ω-hexene, and allyl, preferably vinyl; aryl groups such as phenyl and napthyl; alkaryl groups such as tolyl and xylyl; and arylalkyl groups such as benzyl, and the α- and β-phenylethyl groups. This list is non-limiting.

Examples of substituted non-reactive groups are halo-substituted hydrocarbon groups such as fluorinated and chlorinated hydrocarbon groups, for example, perfluoropropyl, chloropropyl, chloroethyl, o-, m-, and p-chlorophenyl, and the like, and hydrocarbon groups substituted with cyano groups, hydroxyl groups or alkoxy groups (including polyoxyalkylene groups).

The reactive silicones of the present invention contain M units, D units, optionally T units, and optionally Q units, defined as follows:

$$R^1{}_a R_b (OR^2)_c SiO_{1/2} \quad (M)$$

where a, b, and c are each 0 to 3 and the sum of a+b+c is 3;

$$R^1{}_a R_b (OR^2)_c SiO_{2/2} \quad (D)$$

where a, b, and c are each 0 to 2 and the sum of a+b+c is 2;

$$R^1{}_a R_b (OR^2)_c SiO_{3/2} \quad (T)$$

where a, b, and c are 0 or 1 and the sum of a+b+c is 1; and $$SiO_{4/2} \quad (Q).$$

In these formulae, R is a non-reactive group as previously defined, $R^1$ is a reactive functional group which contains an epoxy group, amino group, anhydride group, isocyanate group, carboxylic acid group, or (meth)acrylate group in each case Si—C bonded to silicon; and $OR^2$ is an Si—O bonded alkoxy group, $R^2$ being the same as R.

The reactive silicones may thus be described as $$M_m D_n T_o Q_p$$

where M, D, T, and Q are defined as above, where M is such that all chain ends are terminated with M groups, n is 1 to 10,000, preferably 2 to 1000, and more preferably 2 to 100, o is 0 to 100, preferably 1 to 20, and most preferably 2 to 15; and p is 0 to 10, preferably 0 to 5, and more preferably 0 to 3. Most preferably, the silicones contain no Q units, or only those present as an unavoidable consequence of the hydrolytic condensation. On average, each molecule contains at least two reactive functional groups $R^1$, and the proportion of alkoxy groups, calculated on the basis of methoxy groups, is less than 20 weight percent. By (meth)acrylic group is meant a (meth) acrylic or (meth)acrylate group SiC bound to the organopolysiloxane.

The reactive organopolysiloxanes are generally liquids, for example with a viscosity of 50 cps to $10^6$ cps, more preferably 100 cps to $10^5$ cps, and may be described as lightly to moderately branched organopolysiloxanes, but may not be described as silicone resins, which are highly branched, network like polymers dominated by T and Q groups, and which are generally solids.

The reactive organopolysiloxanes of the present invention are prepared by condensation of alkoxy-functional reactants, optionally also with Si—OH functional polymers. Any suitable method of preparation may be used, but two methods are preferably used. In the first of these methods, which may be termed an ab initio synthesis, the principle reactants are silanes, optionally also using alkoxy-rich partial hydrolysates of these silanes. Each silane contains at least one condensable group, preferably a lower alkyl alkoxy group, more preferably methoxy, ethoxy, or butoxy groups, or mixtures of these. At least one silane contains an Si—C bonded epoxy, isocyanate, anhydride, amino, carboxylic acid, or (meth)acrylate group.

Hereafter, the synthesis will be illustrated for epoxy group-containing reactive organosiloxanes, employing epoxy group-containing reactants, i.e. those containing E groups, and more particularly E'-B-groups as hereafter defined. However, the synthetic methods are equally applicable for isocyanate group-containing reactive organopolysiloxanes, where E and E'-B— are replaced by I and I'—B respectively, amino group-containing reactive organopolysiloxanes where E and E'-B or are replaced by A and A'-B—, anhydride group-containing reactive organopolysiloxanes where E and E'-B are replaced by An and An'-B, respectively, carboxy group-containing reactive organopolysiloxanes where E and E'-B are replaced by Ac and Ac'—B, respectively, and (meth) acrylic group-containing reactive organopolysiloxanes where E and E'-B are replaced by $A_{(m)a}$ and $A'_{(m)a}$-B, respectfully, where I is an isocyanate-containing group, A is an amino-containing group, An is an anhydride containing group, Ac is a carboxy-containing group, and $A_{(m)a}$ is a (meth) acrylic-containing group. It is noted that unless extreme care is taken with respect to reaction conditions, particularly pH, it is generally impossible to prepare reactive organopolysiloxanes containing more than one type of reactive functionality selected from isocyanate, amino, and anhydride, since these groups are generally inter-reactive.

Examples of epoxy-functional silanes are silanes of the formula $$ER_d Si(OR^2)_{(3-d)}$$

where R and $R^2$ have been previously defined, E is an Si—C bonded epoxy group, and d is 0, 1, or 2, preferably 0 or 1.

The group E contains at least one, and preferably only one epoxy group, and may be, for example, aliphatic, cycloaliphatic, arylaliphatic, etc., preferably aliphatic or cycloaliphatic. The E groups are preferably those of the formula E'-B— where F is an epoxy-containing group and B is a $C_1$-$C_{18}$ hydrocarbon group, more preferably a $C_{2-8}$, hydrocarbon group, and most preferably a $C_{2-3}$ hydrocarbon group, or an Si—C bond. The hydrocarbon groups B are preferably aliphatic hydrocarbon groups, preferably methylene, ethylene or propylene groups. F may be, for example an epoxy-substituted aryl compound, but is preferably an aliphatic or cycloaliphatic epoxy compound such as glycidoxy or cyclohexene oxide. Most preferably, E is glycidoxypropyl. These Si—C bonded epoxysilanes are commercially available or may be produced by methods customary in organic and organosilicon chemistry. Two preferred epoxy-functional silanes are 3-glycidoxypropyltrimethoxysilane and 3-glycidoxypropyltriethoxysilane, available as GENIOSIL® GF 80 and GENIOSIL® GF 82 silanes, respectively, from Wacker Chemie, Munich, Germany. To lower alkoxy functionality, the corresponding monoalkoxy or dialkoxy compounds may be used, in this case containing alkyl, cycloalkyl, aryl, arylalkyl, or alkaryl substituents such that silicon is always tetravalent.

Examples of amino-functional silanes

$AR_d(OR^2)_{(3-d)}$, include, for example, N-cyclohexylaminomethylmethyldiethoxysilane, GENIOSIL® XL 924; N-cyclohexylaminomethyltriethoxysilane, GENIOSIL® XL 926; N-phenylaminomethyltrimethoxysilane, GENIOSIL® XL 973; N-(2-aminoethyl)-3-aminopropyltrimethoxysilane, GENIOSIL® GF 9; N-(2-aminoethyl)-3-aminopropyltrimethoxysilane, high purity, GENIOSIL® GF 91; N-cyclohexyl-3-aminopropyltrimethoxysilane, GENIOSIL® GF 92; 3-aminopropyltriethoxysilane GENIOSIL® GF 93; N-(2-aminoethyl)-3-aminopropylmethyldimethoxysilane, GENIOSIL® GF 95; 3-aminopropyltrimethoxysilane, GENIOSIL® GF 96; and 3-ureidopropyltrimethoxysilane, GENIOSIL® GF 98.

Suitable isocyanate-functional silanes

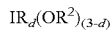
$IR_d(OR^2)_{(3-d)}$ include 3-isocyanatopropyltrimethoxysilane, GENIOSIL® GF 40 and 3-isocyanatomethyltrimethoxysilane, both available from Wacker Chemie, Munich, Germany.

Suitable anyhydride-functional include the hydrosilylation products of unsaturated anhydrides such as maleic anhydride or methylmaleic anhydride with alkoxysilanes such as trimethoxysilane, methyldimethoxysilane, and dimethylmethoxysilane and their ethoxy analogues.

In addition to the functional silanes bearing E, A, An, I, Ac or $A_{(m)a}$ groups, non-functional silanes are also used. These are preferably conventional mono-, di-, tri-, and tetra-alkoxysilanes having the formula

$R_eSi(OR^2)_{(4-e)}$ where R and $R^2$ are as previously defined, and e is 0, 1, 2, or 3. Examples include alkyltrimethoxysilanes, dialkyldimethoxysilanes, and trialkylmethoxysilanes, and their ethoxy analogs; phenyltrimethoxysilane, phenylmethyldimethoxysilane, diphenyldimethoxysilane, diphenlmethylmethoxysilane, phenyldimethylmethoxysilane and their ethoxy analogs, and the like. For increased compatibility with relatively non-polar substances, for example in coatings containing relatively non-polar reactive or non-reactive polymers, the alkyl groups in the alkylalkoxysilanes may be long chain alkyl groups or cycloalkyl groups such as $C_6$-$C_{20}$ alkyl groups, preferably $C_{8-18}$ alkyl groups, and $C_{5-20}$ cycloalkyl groups such as cyclohexyl, methylcyclohexyl, cyclohexylmethyl, norbornyl, and the like. Aryl groups such as napthyl, anthryl, etc. may be present, as well as aryl group-containing compounds such as biphenyl, 4-(phenylmethyl)phenyl, and the like.

The trialkoxysilanes and tetraalkoxysilanes such as tetraethoxysilanes and tetramethoxysilane may be used to impart branching. As indicated previously, highly branched structures are not preferred, as these are generally of high viscosity or are solids, and as the large number of siloxane bonds may make it impossible to achieve a ratio of non-functional groups to silicon of more than 1:1. However, some of the multialkoxy functional compounds may remain in part uncondensed, for example at the polymer terminii or along the polymer chain as alkoxy groups.

To increase the ratio of non-functional R groups to silicon, the molar amounts of trialkoxy and tetralkoxysilanes are reduced, and the amounts of dialkoxysilanes and monoalkoxysilanes are correspondingly increased. The silane mixture is condensed, in one or a plurality of steps, by addition of water, generally with the aid of an acidic or basic condensation catalyst such as an alkali metal hydroxide. Methods and conditions of condensation of silanes are well known in the art. Liberated alcohol is removed, for example as an overhead, and the amount of water collected, e.g. in a cooled condenser, may be used to assess the progress of condensation. Adding greater amounts of water will result in a greater degree of condensation, higher molecular weight, and a reduction in residual alkoxy group content, and the reverse is also true.

When plural steps are used in the synthesis, one or more of the silanes may be partially hydrolyzed to produce an alkoxy-rich intermediate product, which can then be further reacted (hydrolyzed) by itself or with addition of the same or other silanes. Such multistep addition can be used to tailor the polymer structure, and to some degree, the location of the reactive functional groups in the final polymer structure.

In the second preparation method, which is preferred, a preformed, alkoxy-functional organopolysiloxane is employed. This preformed organopolysiloxane may be, for example, a partial hydrolysate of one or more starting silanes. The remaining silanes, water, and catalyst, when required, are added, and further condensation takes place onto the preformed organopolysiloxanes. This method has the advantage of employing readily available, partially condensed organopolysiloxanes having a defined structure, thus being able to more accurately synthesize desired product structures. This method is used in the Examples. Rather than an alkoxy-functional polymer, an α,ω-silanol stopped organopolysiloxanes may be used, either directly, or after reaction with an alkoxysilane to produce alkoxysilyl end groups.

The reactive organopolysiloxanes have numerous uses, for example in coatings, as molded resins, impregnants, hydrophobing compositions, encapsulants, etc. In these uses, the reactive organopolysiloxanes are generally used with a hardener, or curative, or with a curing catalyst.

A "hardener" or "curative" or "curing agent" as used herein is a compound, which may be of low molecular weight, or "monomeric," or oligomeric or polymeric, which provides complementary reactive groups with which the reactive groups of the reactive silicone react. The hardener and reactive organopolysiloxanes may each be of low functionality such that predominately linear chain extension takes place, producing a generally flexible product, or one or both of the hardener or reactive silicone may be of higher functionality such that extensive crosslinking takes place, producing a harder and generally less flexible product.

When the reactive functional group of the reactive organopolysiloxanes is the epoxy group, suitable complementary reactive groups of the hardener are, for example, hydroxyalkyl groups, isocyanate groups, anhydride groups, carboxylic acid groups, primary and secondary amino groups, phenol/formaldehyde condensates, melamine/formaldehyde condensates, and similar condensates, and the like. Such complementary reactive groups are well known in the art of epoxy resins. The hardener may be a "monomeric" organic compound of low molecular weight such as bisphenol A, ethylene glycol, methylenedianiline ("MDA"), etc., or may be oligomeric or polymeric, such as polyethyleneimines or addition polymers containing residues of acrylic acid, methacrylic acid, maleic anhydride, or the like. See, e.g. EPOXY RESINS: CHEMISTRY AND TECHNOLOGY, Clayton May, Ed., Marcel Dekker, © 1988, and HANDBOOK OF EPOXY RESINS, Henry Lee, et al., McGraw-Hill, © 1967.

When the reactive functionality of the reactive organopolysiloxane is isocyanate, complementary reactive groups include primary and secondary amino groups, anhydride groups, epoxy groups, hydroxyalkyl groups, etc. Again, the hardener may be of low molecular weight, or may be an oligomer or polymer. See, e.g. J. H. Saunders, et al., POLYURETHANES CHEMISTRY AND TECHNOLOGY, Interscience Publishers, © 1962.

For amino reactive groups, complementary reactive groups include epoxy groups, isocyanate groups, cyanate groups, anhydride groups, etc., and may be of low or high molecular weight, monomeric, oligomeric, or polymeric.

For each of these systems, it is also possible to use a complementary reactive organopolysiloxane as the hardener. For example, a curable composition with very high silicone content can be created by using an amino-functional organopolysiloxane with either or both of an isocyanate-functional organopolysiloxane and/or an epoxy-functional organopolysiloxanes. Such systems may also contain other hardeners, and may contain a catalyst as well.

Suitable complementary groups for carboxy functionality include isocyanate groups, amino groups, hydroxyl groups, and the like, whereas for (meth)acrylic groups, the complementary groups may be (meth)acrylic groups or other ethylenically unsaturated groups, or Si—H functional silanes and organopolysiloxanes. The (meth)acrylic group-functional organopolysiloxanes may also be cured without a complementary-reactive crosslinker, for example by free radical polymerization using standard free radical initiators such as peroxides, hydroperoxides, azo compounds, or photocatalysts. When Si—H functional crosslinkers or curing agents are used, standard hydrosilylation catalysts, particularly platinum, iridium and rhodium, and their compounds may be used and more particularly platinum and its compounds, for example the Karstedt catalyst.

Isocyanate-functional organopolysiloxanes may in principle also be cured without a complementary crosslinking or curing agent, by adding, for example, an isocyanate condensation catalyst. Such catalysts may, for example, form carbodiimide, uretdione, allophanate, or isocyanurate groups through the reaction of two or more isocyanate groups. Such catalysts are well known from the fields of isocyanates and polyurethanes.

The term "catalyst" as used herein refers to substances which facilitate reaction but are not complementary reactive, e.g. the catalyst is not generally chemically bonded in the cured product, as distinguished by hardeners which do become a substantial part of the product. Epoxy-functional, isocyanate-functional, and (meth)acrylate-functional systems may all be catalyzed. For epoxy systems, suitable catalysts are those known in the art, and include acids, bases, and tertiary amines, as well as a variety of metal compounds, both organic and inorganic. For isocyanates, tin and bismuth catalysts are often used with hydroxyl-functional hardeners, and tertiary amines, phosphorous-containing catalysts and metal catalysts may be used to dimerize isocyanate groups into carbodiimide groups, or to trimerize isocyanates into isocyanaturate structures. While amino-functional and anhydride-functional organopolysiloxanes generally require a hardener to cure, epoxy- and isocyanate-functional organopolysiloxanes may be cured catalytically without use of a hardener, as may also (meth)acrylate-functional organopolysiloxanes.

The curable compositions may also contain non-reactive polymers, generally film forming polymers, and may produce homogenous cured compositions or interpenetrating polymer network compositions. By the term "non-reactive polymers" is meant polymers which have no complementary reactive groups or such a low concentration of such groups that a solid, cured composition cannot be obtained without the use of either or both of a separate hardener or catalyst. Examples of such polymers are polyvinylacetate, polyvinyl chloride, other polyvinyl ester polymers, polyacrylates, including polyacrylates with a very small proportion of residual unsaturated acrylic acid or methacrylic acid groups, polyvinyl acetals, polycarbonates, polyether sulfones, polyurethanes, polyureas, polyamides, and the like. It is preferred that the non-reactive polymers have a very minor amount of reactive groups so that despite being unable to cure the composition, the polymer becomes covalently bonded within the composition.

Curable compositions which comprise the reactive organopolysiloxanes may take numerous forms. They may contain a condensation catalyst in an amount effective to polymerize the organopolysiloxanes through a single kind of reactive group. Examples of such compositions include reactive organopolysiloxanes bearing isocyanate groups, epoxy groups, or (meth)acrylic groups.

The compositions may also include a reactive organopolysiloxane and a compound which reacts with the reactive functional groups of the reactive organopolysiloxanes, i.e. contains complimentary reactive groups. The compound containing the complimentary reactive groups may be a monomeric, oligomeric, or polymeric organic compound, or may be a complementary reactive organosilane or oligomeric or polymeric organopolysiloxane, including silicone resins. The complimentary reactive organopolysiloxanes themselves may be a reactive organopolysiloxane as disclosed herein, or may be a non-inventive organopolysiloxane, for example one containing more than 20 weight percent alkoxy groups, or containing no alkoxy groups. One example of the latter are the commercially available aminoalkyl-functional organopolysiloxanes where the amino alkyl groups may be terminal, pendant, or both terminal and pendant.

The curable compositions may also contain non-inventive organopolysiloxanes bearing the same type of reactive group as the inventive organopolysiloxane, or monomeric, oligomeric, or polymeric organic compounds bearing the same type of reactive functional group. One example of such a curable system, for example, might include as a first reactive component an inventive epoxy-functional reactive organopolysiloxane and a bisphenol A-type epoxy resin, and as a second component an aminoalkyl-functional organopolysiloxane, a di- or polyamine, or a mixture of these. Such mixtures are made possible by the inventive reactive organopolysiloxanes which have high compatibility with other purely organic or substantially purely organic compounds.

When catalysts are used, these are advantageously formulated as a second component. It is possible, for example, to provide the catalyst dissolved or dispersed in a suitable solvent, in an organopolysiloxane, including non-reactive organopolysiloxanes which may serve as an extender or plasticizer, in a paraffinic or naphthenic oil, or the like. In some cases, when the catalyst is activatable only at elevated temperature, or when an inhibitor is present, or in aqueous compositions where reaction takes place only after evaporation of water or after coalescence of the organic (including organosilicon) phase, the catalyst may be included in the composition, resulting in a one component system.

The curable compositions may be "neat" in the sense that they contain no solvent or are not in the form of a dispersion, e.g. an aqueous dispersion, or may be formulated with a solvent or dispersing liquid. Preferable solvents are those with a low global warming potential such as tertiarybutylacetate, but conventional solvents such as alcohols, ethers, esters, paraffinic hydrocarbons, and aromatic solvents such as toluene and xylene may also be used.

The reactive organopolysiloxanes may be prepared and used as an aqueous dispersion, with or without additional ingredients. In such cases, dispersions may be prepared by using high shear mixers, generally with the aid of a surfactant. For storage stable compositions, a surfactant which does not bear complementarily reactive groups and which does not function as a catalyst is preferably selected. Anionic, cationic, and zwitterionic catalysts may be used, depending upon the nature of the reactive organopolysiloxanes, but non-ionic surfactants such as polyoxyalkylated glycols or alcohols are preferred. The curable compositions are generally two-component compositions in which each component simultaneously does not include the reactive organopolysiloxanes and hardener or catalyst.

The curable compositions may include numerous additives, including antistats, fragrances, biocides, dyes, pigments, fillers, UV and/or thermal stabilizers, coalescing agents, glossing agents, flattening agents, plasticizers, electrically conducting additives such as carbon black, adhesion promoters, hydrophobing agents such as waxes, silicone oils, and fluorine-containing compounds, and other additives generally used.

When used as coatings, plural component compositions, particularly two component compositions are preferably employed. One component, for example, may contain the reactive organopolysiloxane and other non-reactive components such as dyes, pigments, non-reactive polymer, etc., dispersed in water, and a second component may contain catalyst and/or hardener, reactive or non-reactive polymer, dyes, pigments, etc. The components are mixed prior to use, and applied to a substrate by any suitable method, including brushing, spraying, dipping, roll coating, doctor blade coating, curtain coating, and the like, and are then allowed to dry and cure. Cure, and optionally drying, advantageously take place at elevated temperature, e.g. up to 350° C., preferably no more than 250° C., and yet more preferably no more than 200° C.

In some preferred compositions, it is desirable to reduce or eliminate the use of epoxy-functional trialkoxysilanes, and to use epoxy-functional dialkoxysilanes. It has been surprisingly and unexpectedly discovered that cured polymers prepared from inventive organopolysiloxane polymers synthesized in this way, although exhibiting reduced hardness, achieve maximum hardness faster than when the functional organopolysiloxane is prepared using trialkoxysilanes. In addition, volatiles are reduced by about 33%. Such compositions are well suited for encapsulation or the preparation of thick moldings. Preferred systems of this nature include an aminoalkyl-functional organopolysiloxane free of alkoxy groups, and an inventive epoxysiloxane.

In the examples described below, all parts and percentages are, unless indicated otherwise, by weight. Unless indicated otherwise, the following examples are carried out at the pressure of the surrounding atmosphere, i.e. at about 1000 hPa, and at room temperature, i.e. at about 20° C., or at a temperature which is established on combining the reactants at room temperature without additional heating or cooling. In the following, all viscosities relate to the dynamic viscosity at a temperature of 20° C. and a shear rate 1 The following examples illustrate the invention without having a limiting effect.

EXAMPLES

Examples 1-3

Alkoxy-functional organopolysiloxane, non-functional silane, and 3-glycidoxypropyltrimethoxy silane are charged to a 500 ml reaction flask and blanketed with nitrogen gas. To begin hydrolytic condensation, aqueous 45% KOH was slowly added, and then water. The contents were stirred without heating for 15 minutes, following which the temperature was increased to 78° C. The reaction mixture was refluxed at 78° C. until the appropriate amount of alcohol was collected in a cooled trap. The charges and product properties are reported in Table 1.

TABLE 1

| Charge to 500 ml reaction flask | | | |
|---|---|---|---|
| Alkoxy functional siloxane (Wacker SILRES ® SY231)[1] | 198.36 | 131.95 | |
| Dimethoxydimethyl silane | | | 219.04 |
| 3-glycidoxypropyl dimethoxymethyl silane | 201.64 | 268.05 | |
| 3-glycidoxypropyl trimethoxy silane | | | 139.10 |
| 45% KOH (aq) | 0.18 | 0.18 | 0.48 |
| Water | 9.05 | 12.17 | 41.38 |
| Reflux @ 78° C. until appropriate amount of alcohol has been collected | −31.18 | −41.93 | −143.56 |
| Appearance | v. sl. amber | v. sl. amber | amber |
| Viscosity (#3 RVT @ 20 rpm) | 65 | 40 | 435 |

[1]SILRES ® SY231 is a methoxy/butoxy-functional methyl/phenyl organopolysiloxane containing about 20 weight percent alkoxy groups, available from Wacker Chemical Corp., Adrian, Michigan.

Examples 4-12

Following the procedure of Examples 1-3, additional reactive silicones were prepared. The starting materials and amounts, in percentage by weight, and the epoxy and alkoxy contents of the final products in weight percent are presented in Table 2.

TABLE 2

| Example | 4 | 5 | 6 | 7 | 8 | 9 | 10 | 11 | 12 |
|---|---|---|---|---|---|---|---|---|---|
| Alkoxy functional siloxane I[1] | 0.17 | 0.10 | 0.17 | 0.19 | | | | | 0.19 |
| Alkoxy functional siloxane II[2] | | | | | | 0.18 | | | |
| Alkoxy functional siloxane III[3] | | | | | 0.20 | | | | |
| Dimethoxydimethyl silane | | | | | | | 0.33 | 0.76 | |
| 3-glycidoxypropyl trimethoxy silane | | | | | | | 0.67 | 0.24 | |
| 3-glycidoxypropyl dimethoxymethyl silane | 0.83 | 0.90 | | | | 0.82 | | | |
| 3-glycidoxypropyl diethoxymethyl silane | | | 0.83 | 0.81 | 0.80 | | | | |
| 3-glycidoxypropyl dimethylethoxy silane | | | | | | | | | 0.81 |

TABLE 2-continued

| Example | 4 | 5 | 6 | 7 | 8 | 9 | 10 | 11 | 12 |
|---|---|---|---|---|---|---|---|---|---|
| Water | | 0.45 | 0.50 | 0.45 | 0.50 | 0.50 | 0.45 | 1.20 | 0.95 | 1.17 |
| % Epoxy | | 10.42 | 14.14 | 9.76 | 9.25 | 9.25 | 10.42 | 19.76 | 9.83 | 11.05 |
| % Alkoxy | | 16.05 | 15.27 | 19.11 | 17.98 | 18.25 | 14.95 | 5.76 | 9.85 | >2% |

[1] Alkoxy functional siloxane I is SILRES ® SY231 is a methoxy/butoxy-functional methyl/phenyl organopolysiloxanes containing about 20 weight percent alkoxy groups, available from Wacker Chemical Corp., Adrian, Michigan.
[2] Alkoxy functional siloxane II is a methoxy-functional methyl/phenyl organopolysiloxane containing 16 weight percent methoxy groups, and available as SILRES ® IC232 from Wacker Chemical Corp., Adrian, Michigan.
[3] Alkoxy-functional siloxane III is a methoxy functional methyl organopolysiloxane having 30 weight percent methoxy groups, available as SILRES ® MSE 100 from Wacker Chemical Corp., Adrian, Michigan.

Comparative Examples 1 and 2 and Examples 13-17

Coatings were prepared from the inventive reactive silicones from Examples 4, 5, 9, 11, and 12, and from a commercially available epoxy and alkoxy-functional methyl/phenyl organopolysiloxane having terminal glycidoxypropyl groups and an alkoxy content of 22 weight percent, designated as "commercial epoxy siloxane". The results are presented in Table 3. The reactive silicones were formulated with a carboxy-functional acrylic polymer, PARALOID™ AE-1285, available from Dow Chemical Corporation, Midland, Mich.

| | Eq. Wt. | System 1 | System 2 |
|---|---|---|---|
| Alkoxy-free aminosiloxane | 260 | 9.4 | 9.8 |
| Epoxysiloxane 1 (made using 3-glycidoxy trimethoxy silane) | 432 | 15.6 | |
| Epoxysiloxane 2 (made with 3-glycidoxypropyl dimethoxymethyl silane) | 402 | | 15.2 |
| König hardness - 7 days | | 57 | 29 |
| König hardness - 7 days in nitrogen | | 29 | 30 |
| König hardness - 14 days | | 73 | 29 |
| König hardness - 14 days in nitrogen | | 33 | 31 |

TABLE 3

| Example | C1 | C2 | 13 | 14 | 15 | 16 | 17 |
|---|---|---|---|---|---|---|---|
| Commercial Epoxy Siloxane (Current Technology) | 3.20 | | | | | | |
| Commercial Epoxy Siloxane (Current Technology) | | 2.50 | | | | | |
| Epoxy Siloxane 4 | | | 3.02 | | | | |
| Epoxy Siloxane 5 | | | | 2.35 | | | |
| Epoxy Siloxane 9 | | | | | 3.02 | | |
| Epoxy Siloxane 11 | | | | | | 1.76 | |
| Epoxy Siloxane 12 | | | | | | | 3.16 |
| Carboxy Functional Acrylic | 11.80 | 12.50 | 11.98 | 12.65 | 11.98 | 13.24 | 11.84 |
| DTT | <45' | <45' | <45' | <45' | <45' | <45' | <45' |
| König Hardness (72 hrs @ 70° F./30% RH) | 55.3 | 54.8 | 39.3 | 42.7 | 41.0 | 16.3 | 19.0 |

As can be seen from the Table, despite having a low functionality which would be expected to form a flexible coating, the commercial epoxy-functional siloxane, which had less than 1 non-reactive alkyl group per silicon atom, produced only hard coatings, indicating that a substantial degree of crosslinking was due to reaction of alkoxy groups. The inventive reactive silicones were able to provide both hard and soft (flexible) coatings.

Examples 18 and 19

Alkoxy free organopolysiloxanes bearing aminoalkyl groups were reacted with inventive epoxy-functional organopolysiloxanes containing alkoxy groups (less than 20% by weight) and allowed to cure. One epoxy-functional organopolysiloxane was prepared from 3-glycidoxytrimethoxysilane while the other was prepared from 3-glycidoxydimethoxymethylsilane. The epoxy equivalent weights were similar but not identical. The results are presented below:

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A reactive organopolysiloxane prepared by hydrolytic condensation, containing on average
   a) at least two reactive functional groups per molecule, selected from the group consisting of epoxy, isocyanate, anhydride, amino, carboxy, and (meth)acrylate groups, and mixtures thereof, the functional groups SiC-bonded to silicon atoms in the reactive organopolysiloxanes, and
   b) alkoxy groups, in a concentration of from 1 weight percent to less than 20 weight percent based on the total weight of the reactive organopolysiloxanes, calculated on the basis of methoxy groups, and c) non-reactive optionally substituted hydrocarbon groups Si—C bonded to silicon atoms of the reactive organopolysiloxane, the non-reactive optionally substituted hydrocarbon groups present in a ratio of ≥1.1 and less than 1.5 hydrocarbon groups per atom of Si in the reactive organopolysiloxane, wherein the reactive organopolysiloxane is a non-resinous liquid, linear organopolysiloxane having a viscosity of from 50 cps to $10^6$ cps.

2. The reactive organopolysiloxane of claim 1, wherein the weight percent of alkoxy groups is between 1% and 18%.

3. The reactive organopolysiloxane of claim 1, wherein the weight percent of alkoxy groups is between 2% and 15%.

4. The reactive organopolysiloxane of claim 1, wherein the reactive functional groups are selected from the group consisting of epoxy groups, isocyanate groups, amino groups, and anhydride groups.

5. The reactive organopolysiloxanes of claim 1, wherein the reactive functional group are selected from the group consisting of epoxy groups.

6. A curable composition, comprising
   a) a reactive organopolysiloxane of claim 1, bearing reactive groups selected from the group consisting of isocyanate, epoxy, and methacrylate groups, and a catalyst effective to cause condensation of the respective functional groups, or
   b) a reactive organopolysiloxane of claim 1 and at least one curing agent bearing complementary reactive functional groups reactive with the reactive functional groups of the reactive organopolysiloxane of claim 1, and optionally a catalyst effective to catalyze the reaction of the reactive functional groups with the complementary reactive functional groups; or
   c) a first reactive organopolysiloxane of claim 1 and a second reactive organopolysiloxane of claim 1 bearing complementarily reactive functional groups reactive with the reactive functional groups of the first reactive organopolysiloxane, and optionally a catalyst effective to catalyze the reaction of the reactive functional groups of the first reactive organopolysiloxanes with the second reactive organopolysiloxane.

7. The curable composition of claim 6 which is a composition a).

8. The curable composition of claim 6 which is a composition b).

9. The curable composition of claim 6 which is a composition c).

10. The curable composition of claim 6, comprising a reactive organopolysiloxane bearing reactive functional groups selected from the group consisting of isocyanate groups and epoxy groups, and at least one compound bearing aminoalkyl groups.

11. The curable composition of claim 10, wherein the compound bearing aminoalkyl groups comprises an aminoalkyl-functional organopolysiloxane bearing substantially no alkoxy groups.

12. The curable composition of claim 6, wherein a reactive organopolysiloxane bears (meth)acrylate groups, and the composition
   i) further comprises a free radical initiator effective to polymerize the (meth)acrylate groups, or
   ii) further comprises an Si—H functional crosslinker and an effective amount of a hydrosilylation catalyst.

13. A process for the preparation of a reactive organopolysiloxane of claim 1, comprising
   a) condensing a plurality of alkoxysilanes or their partial hydrolysates, at least one first alkoxysilane or first partial hydrolysate bearing a reactive functional group, and at least one second alkoxysilane or second partial hydrolysate bearing 1, 2, or 3 non-reactive, optionally substituted hydrocarbon groups, wherein the alkoxy functionality of the first and second alkoxysilanes and/or partial hydrolysates thereof are selected, together with the degree of completion of condensation, to provide a reactive organopolysiloxane with at least two reactive functional groups, an alkoxy content of less than 20 weight percent, and a ratio of optionally substituted non-reactive hydrocarbon groups to silicon atoms of ≥1.1 and less than 1.5, or
   b) condensing a silanol-stopped or alkoxysilyl-stopped organopolysiloxane with a reactive group-containing silane or partial hydrolysate thereof, optionally also with an alkoxysilane bearing 1, 2, or 3 non-reactive, optionally substituted hydrocarbon groups, wherein the alkoxy functionality of the first and second alkoxysilanes and/or partial hydrolysates thereof are selected, together with the degree of completion of condensation, to provide a reactive organopolysiloxane with at least two reactive functional groups, an alkoxy content of less than 20 weight percent, and a ratio of optionally substituted non-reactive hydrocarbon groups to silicon atoms of ≥1.1 and less than 1.5.

14. The process of claim 13, wherein the reactive group-containing silane is selected from the group consisting of reactive group-containing trialkoxysilanes, reactive group-containing dimethoxysilanes, and mixtures thereof.

15. The process of claim 14, wherein the reactive group-containing silane is an epoxyalkyldialkoxymethylsilane.

16. A reactive organopolysiloxane prepared by hydrolytic condensation, containing on average
   a) at least two reactive epoxy functional groups per molecule, the reactive epoxy functional groups SiC-bonded to silicon atoms in the reactive organopolysiloxanes, and
   b) alkoxy groups, in a concentration of from 1 weight percent to less than 20 weight percent based on the total weight of the reactive organopolysiloxanes, calculated on the basis of methoxy groups, and
   c) non-reactive optionally substituted hydrocarbon groups Si—C bonded to silicon atoms of the reactive organopolysiloxane, the non-reactive optionally substituted hydrocarbon groups present in a ratio of >1 hydrocarbon group per atom of Si in the reactive organopolysiloxane, wherein the reactive organopolysiloxane is a non-resinous liquid, linear organopolysiloxane having a viscosity of from 50 cps to $10^6$ cps.

17. The reactive organopolysiloxane of claim 16, wherein the ratio of non-reactive optionally substituted hydrocarbon groups to silicon atoms is ≥1.1 and less than 2.

18. The reactive organopolysiloxane of claim 16, wherein the ratio of non-reactive optionally substituted hydrocarbon groups to silicon atoms is ≥1.1 and less than 1.5.

19. A curable composition, comprising
   a) a reactive organopolysiloxane of claim 16, and a catalyst effective to cause condensation of the epoxy functional groups, or
   b) a reactive organopolysiloxane of claim 16 and at least one curing agent bearing complementary reactive functional groups reactive with the reactive epoxy functional groups of the reactive organopolysiloxane of claim 16, and optionally a catalyst effective to catalyze the reaction of the epoxy groups with the complementary reactive functional groups; or
   c) a first reactive organopolysiloxane of claim 16 and a second reactive organopolysiloxane bearing complementarily reactive functional groups reactive with the reactive epoxy functional groups of the first reactive organopolysiloxane, and optionally a catalyst effective to catalyze the reaction of the reactive epoxy functional groups of the first reactive organopolysiloxanes with the second reactive organopolysiloxane.

20. A process for the preparation of a reactive organopolysiloxane of claim 16, comprising
   a) condensing a plurality of alkoxysilanes or their partial hydrolysates, at least one first alkoxysilane or first partial hydrolysate bearing a reactive epoxy functional group, and at least one second alkoxysilane or second partial hydrolysate bearing 1, 2, or 3 non-reactive, optionally substituted hydrocarbon groups, wherein the alkoxy functionality of the first and second alkoxysilanes and/or partial hydrolysates thereof are selected, together with the degree of completion of condensation, to provide a reactive organopolysiloxane with at least two reactive epoxy functional groups, an alkoxy content of less than 20 weight percent, and a ratio of optionally substituted non-reactive hydrocarbon groups to silicon atoms of >1, or
   b) condensing a silanol-stopped or alkoxysilyl-stopped organopolysiloxane with a reactive epoxy group-containing silane or partial hydrolysate thereof, optionally also with an alkoxysilane bearing 1, 2, or 3 non-reactive, optionally substituted hydrocarbon groups, wherein the alkoxy functionality of the first and second alkoxysilanes and/or partial hydrolysates thereof are selected, together with the degree of completion of condensation, to provide a reactive organopolysiloxane with at least two reactive epoxy functional groups, an alkoxy content of less than 20 weight percent, and a ratio of optionally substituted non-reactive hydrocarbon groups to silicon atoms of >1.

* * * * *